US007736638B2

(12) United States Patent
Savio et al.

(10) Patent No.: US 7,736,638 B2
(45) Date of Patent: Jun. 15, 2010

(54) INTERLEUKIN-15 ANTAGONIST PEPTIDE

(75) Inventors: Alicia Santos Savio, Ciudad de La Habana (CU); Ania Cabrales Rico, Ciudad de La Habana (CU); Osvaldo Reyes Acosta, Ciudad de La Habana (CU); Haydee Geronimo Perez, Ciudad de La Habana (CU); Celia Aurora Arrieta Aguero, Ciudad de La Habana (CU); Silvio Ernesto Perea Rodriguez, Ciudad de La Habana (CU)

(73) Assignee: Centro de Ingenieria Genetica y Biotecnologia, C. Habana (CU)

( * ) Notice: Subject to any disclaimer, the term of this patent is extended or adjusted under 35 U.S.C. 154(b) by 88 days.

(21) Appl. No.: 11/662,844

(22) PCT Filed: Sep. 16, 2005

(86) PCT No.: PCT/CU2005/000007

§ 371 (c)(1),
(2), (4) Date: Sep. 30, 2008

(87) PCT Pub. No.: WO2006/029578

PCT Pub. Date: Mar. 23, 2006

(65) Prior Publication Data

US 2009/0136511 A1    May 28, 2009

(30) Foreign Application Priority Data

Sep. 17, 2004    (CU) .................................. 2004-0198

(51) Int. Cl.
A61K 38/20     (2006.01)
C12N 15/06     (2006.01)
C07K 14/54     (2006.01)
C12N 5/02      (2006.01)
C12P 21/02     (2006.01)

(52) U.S. Cl. .................. 424/85.2; 530/351; 514/12; 435/69.5; 435/320.1; 536/23.5

(58) Field of Classification Search ........................ None
See application file for complete search history.

(56) References Cited

U.S. PATENT DOCUMENTS 5,894,018 A    4/1999 Davia et al.
6,013,480 A    1/2000 Grabstein et al.
6,344,192 B1   2/2002 Grooten et al.

FOREIGN PATENT DOCUMENTS

EP    0927254          6/2005
WO    WO 95/27722 A1   10/1995
WO    WO9604306    *   2/1996
WO    WO0002582 A      1/2000
WO    WO01/02003       1/2001
WO    WO2005/085282    9/2005

OTHER PUBLICATIONS

Lazar et al, Mol. Cell. Biol., 1988, vol. 8, pp. 1247-1252.*
Wells, 1990, Biochemistry 29:8509-8517.*
Silva et al, Inflammatory bowel disease, Mar. 2005, vol. 11, No. 3, pp. 219-230.*
Crystal, R. Science, 1995, vol. 270, pp. 404-410.*
Verma et al. Nature, 1997, vol. 389, p. 239-242.*
Ross et al, Human Gene Therapy, 1996, vol. 7, pp. 1781-1790.*
Rubanyi, Biol. Aspects Med. 2001, vol. 22, pp. 113-142.*
I. B. McInnes, Book Series: Ernst Schering Foundation Symposium Proceedings, Publisher: Springer Berlin Heidelberg, 2006, vol. 56, pp. 29-44.*
Bernard J., et al., "Identification of an Interleukin-15 Alpha Receptor-Binding Site on Human Interleukin-15", Journal of Biological Chemistry, American Society of Biochemical Biologists, vol. 279, No. 23, pp. 24313-24322 (Jun. 4, 2004).
Fehniger T.A. et al., "Interleukin 15: Biology and Relevance to Human Disease", Blood, W.B. Saunders Company, vol. 97, No. 1, pp. 14-32 (Jan. 1, 2001).
Brewer JM et al., "Aluminum Hydroxide Adjuvant Initiates Strong Antigen-Specific Th2 Responses in the Absence of IL-4- or IL-13-mediated Signaling", J. Immunol, vol. 163:6448-6454 (1999).
Gonzalez, S. et al., "P64k Meningococcal Protein as Immunological Carrier for Weak Immunogens", Scan J. Immunol. vol. 52, p. 113-116 (2000).
Schwartz RH and Muller DL, Immunological Tolerance. In Fundamental Immunology, 5th Ed. W.E. Paul (Ed)., Lippincott, Williams, and Wilkins p. 901-934 (2003).
Al-Mughales J. et al., "The Chemoattractant Activity of Rheumatoid Synovial Fluid for Human Lymphocytes is Due to Multiple Cytokines", Clin. Exp. Immunol. vol. 106: 230-236 (1996).
Obermeier F. et al., "IL-15 Protects Intestinal Epithelial Cells", Eur. J. Immunol, vol. 36: 2691-2699 (2006).
Kukita T. et al., "Autocrine and/or Paracrine Growth of Adult T-Cell Leukaemia Tumour Cells by Interleukin 15", Br. J. Haematol., vol. 119:467-474 (2002).

* cited by examiner

*Primary Examiner*—Bridget E Bunner
*Assistant Examiner*—Fozia M Hamud
(74) *Attorney, Agent, or Firm*—Hoffmann & Baron, LLP

(57) ABSTRACT

Current invention is related to the molecular pharmacology branch particularly to a peptide belonging to the Interleukin-15 sequence (IL-15) which is able to inhibit IL-15 biological activity, analogues or mimetic of such peptides. In the current invention it is shown that the peptide inhibits both IL-15-induced T cells proliferation upon binding to the IL15 receptor a subunit (IL15Rα) and TNFα-mediated apoptosis.

Figure 3:
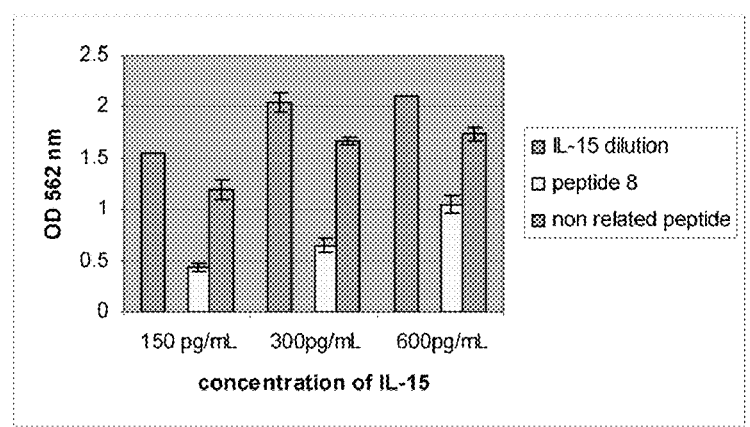
Figure 3:
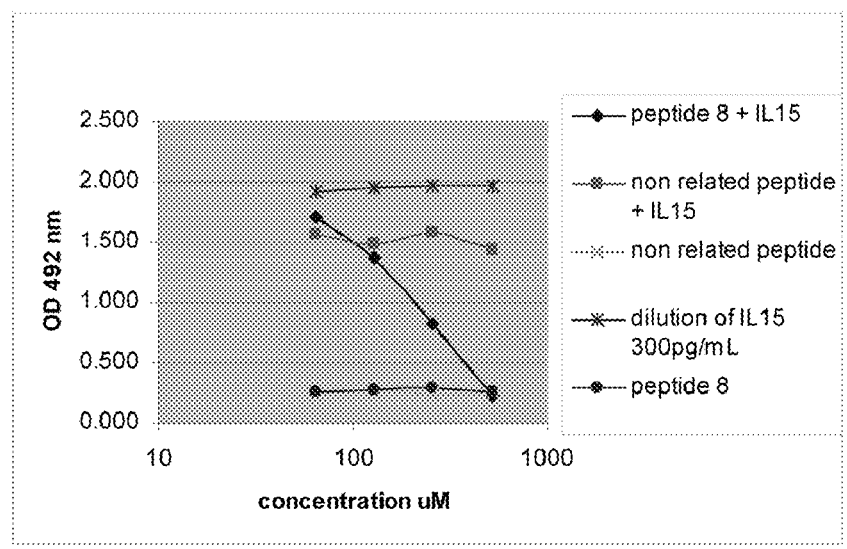

Besides, this invention is related to the use of this peptide in the treatment of several pathologies where aberrant IL-15 or IL-15Rα expression is associated to the disease progression.

9 Claims, 3 Drawing Sheets

Figure 1:
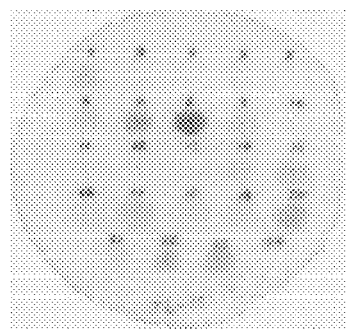
Figure 2:
Fig 2a
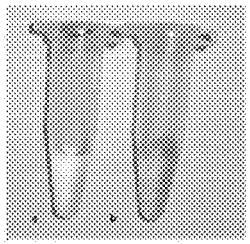
a) Non-related peptide
b) Peptide having the amino acid sequence set forth in SEQ ID NO: 1
Fig 2b
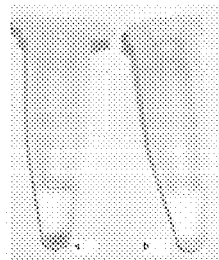
a) Peptide having the amino acid sequence set forth in SEQ ID NO: 1
b) Peptide having the amino acid sequence set forth in SEQ ID NO: 1, plus IL-15

3a )

3b )

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Lys Val Thr Ala Met Lys Cys Phe Leu Leu
1               5                   10
```

INTERLEUKIN-15 ANTAGONIST PEPTIDE

This application is the U.S. National Phase of, and Applicants claim priority from, International Application Number PCT/CU2005/000007 filed 16 Sep. 2005 and Cuban Patent Application bearing Serial No. CU 2004-0198 filed 17 Sep. 2004, which are incorporated herein by reference.

FIELD OF INVENTION

The current invention is related to the branch of molecular pharmacology particularly to a peptide from Interleukin-15 (IL-15) which impairs IL-15 binding to the receptor alpha subunit; therefore, it could be useful for treatment of diseases associated with aberrant expression of IL-15 or IL-15Rα.

PREVIOUS ART

The cytokine known as IL-15 is a 14-15 kDa glycoprotein simultaneously identified by two groups as a T cell-activating factor (Grabstein, K. H. et al., Science 1994, 264, 965; Burton, J. D. et al., Proc. Natl. Acad. Sci, USA 1994, 91, 4935). IL-15 mRNA is widely expressed in different cells and tissues, however, it is difficult to find the protein in these cells or in the cells supernatant due to a strong post-transcriptional control of its expression at the translational level and the intracellular traffic (Bamford R N. et al., J. Immunol. 1998, 160: 4418-4426; Kurys G, et al., J. Biol. Chem. 2000, 275: 30653-30659). Moreover, it has been shown that IL-15 may exist in an active form as a membrane protein (Musso et al., Blood 1999, Vol. 93, No 10 (May 15),: pp 3531-3539) and recently was noted that it may function either as ligand or as receptor (Budalgian et al., JBC 2004, vol 279, No 40: pp 42192-42201) inducing through this pathway secretion of pro-inflammatory cytokines.

High expression level of the soluble protein has been associated to the pathogenesis of auto-immune and inflammatory diseases. IL-15 has been detected in several diseases including Crohn's disease (Kirman I., 1996, Am. J. Gastroenterol. 91, 1789), Psoriasis (Rückert R. 2000, 165: 2240-2250), Leukemias (Yamada Y. 1999, Leukemia and Lymphoma, 35(1-2): 37-45 and Rheumatoid Arthritis (RA), (McInnes I. B. 1998, Immunology Today, 19, 75-79). Binding of the ligand to the T cell receptor induces expression of IL-15Rα and expression of several activation antigens such as CD69, CD25 and TNFRII. Also IL-15 is a chemoattractant for human blood T lymphocytes (Wilkinson 1995, J. Exp. Med. 181, 1255-1259). All these data suggest that IL-15 expressed by antigen presenting cells could be important on the early T cell activation at the inflammation site.

McInnes et al., found IL-15 expression abnormalities in this disease, high IL-15 concentration in the synovial fluid and its expression in synovial membrane cells. They suggested that IL-15 precedes TNFα in the cytokine cascade, proposing a mechanism dependent on cell contact, where, IL-15 activated T cells induce TNFα synthesis by macrophages. Moreover, it is proposed that IL-15 acts as an important factor on the T cell migration to the synovial fluid (McInnes, 1997, Nat Med, 3: 189-195).

Ziolkowska et al., reported that IL-15 induces IL-17 expression at joints from RA patients, it is already known that this cytokine stimulates release by synoviocytes of several inflammatory mediators such as IL-6, IL-8, GM-CSF, and prostaglandin E2 suggesting an important role for IL-15 in the RA pathogenesis (Ziolkowska y col 2000, J Immunol, 164: 2832-2838).

T cells recruitment and activation may occur as a consequence of IL-15 local synthesis and such non specific activation could bring as a result an endless inflammation. All this suggest that IL-15 inhibition could have a therapeutic potential on the disease treatment as well as other auto-immune and inflammatory diseases.

The IL-15 biological effects are mediated through its binding to a cell membrane receptor composed of three subunits α, β, and γ. The IL-15Rα is a specific subunit for this cytokine to whom is bound with a very high affinity Kd $10^{-11}$, and may be found as a membrane receptor or in a soluble form (Budagian V. et al., JBC 2004, 279, 39: 40368-40375; Mortier et al., The Journal of Immunology, 2004, 173: 1681-1688).

Subunits β and γ are shared with IL-2, a cytokine with a high structural homology to IL-15. It has been previously described that Asp56 in the IL-15 molecule is important in the binding to the receptor β subunit and Gln156 is important in the binding to receptor γ subunit Muteins behave like IL-15 antagonists molecules bound to the receptor α subunit and impair signal transduction through β and γ subunits. Antibodies which recognizes these amino acids, also act as IL-15 antagonists (U.S. Pat. No. 6,177,079, U.S. Pat. No. 6,168,783, U.S. Pat. No. 6,013,480, U.S. Pat. No. 6,001,973, U.S. Pat. No. 9,706,931, WO9741232).

Ruchatz et al. (Ruchatz H. 1998, J. Immunol. 160: 5654-5660) generated a soluble fragment of the murine α receptor subunit (IL-15Rα) and demonstrated that injection of this fragment inhibited collagen-induced artritis (CIA) in DBA/1 mice.

Genmab Company owes the Patent of specific human antibodies against IL-15, WO03017935, where 4 antibodies are described and 2 of them, 146B7 and 146H5 bind to IL-15 in the receptor α subunit interacting region and inhibit IL-15-induced cell proliferation in the cell line CTLL2 and in PBMC (peripheral blood mononuclear cells), and antibodies 404A8 and 404E4 which do not inhibit proliferation. The 146B7 antibody (Amgen) under the name AMG714 is in Rheumatoid Arthritis Clinical Trials Phase II.

Recently, two IL-15 binding sequences to the receptor α subunit were identified, from amino acid 44 to 52 and from amino acid 64 to 68 (Bernard et al., JBC 2004, 279 (23), 24313-24322). They described muteins which can act either as IL-15 agonist or antagonist.

So far, it has not been described any IL-15 antagonist peptide. Use of a short length peptide (10 aa) as an IL-15 antagonist has the advantage to selectively block IL-15 binding to receptor α subunit and mediate or impair IL-15 effects due to IL-15-receptor interaction. For example, as described in current invention, peptide named Sec. No.1 spans a 10 amino acids region of IL-15 which we identified as the interacting region with the receptor α subunit (FIG. 1). Such peptide binds IL-15Rα-Fc fusion protein in ELISA and in Tentagel resin assay (FIG. 2), inhibits IL-15-dependent CTLL-2 cell line proliferation (FIGS. 3a and 3b), and protects from TNFα-induced apoptosis (FIG. 4), this effect is mediated by IL-15 binding to the receptor α chain. This latter effect allows its use in diseases where it is necessary to inhibit the apoptotic process. Likewise, the binding of this peptide to the soluble chain α as described in current invention may inhibit reverse signalling mediated by membrane-associated IL-15 (Budalgian et al., JBC 2004, vol 279, No 40: pp 42192-42201).

DETAILED OF INVENTION DESCRIPTION

Figure 4:
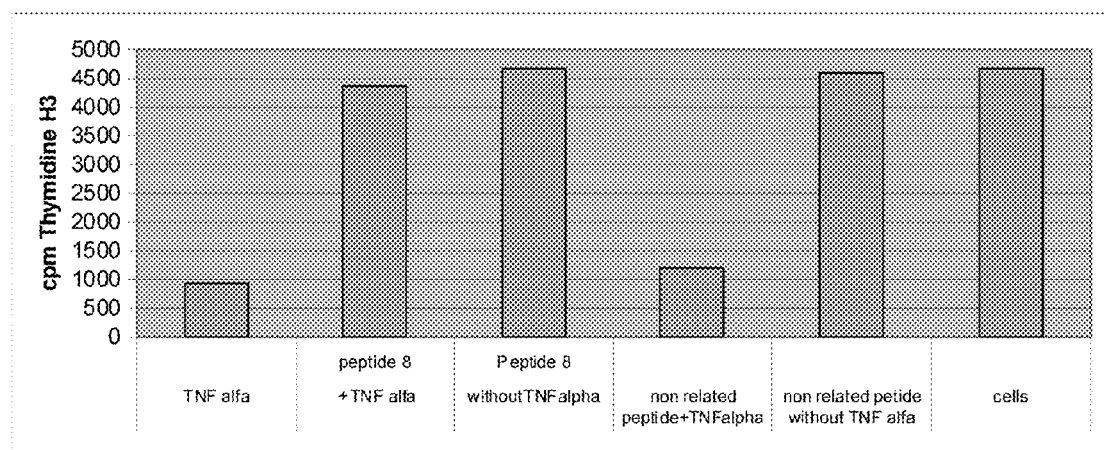

Particularly, this invention is referred to identification of an IL-15 region which is capable to bind IL-15Rα subunit. The peptide comprising this region here named Sec. No. 1 was chemically synthesized and has binding capacity to IL-15 Rα-Fc (FIG. 2), inhibits IL-15-induced CTLL2 proliferation and protects from TNFα-induced DNA fragmentation (FIG. 4).

This invention also includes any homologue or mimetic variants of former peptide which have been obtained by recombinant or synthetic approaches as well as any formulation containing them.

Likewise, this invention also includes the use of the afore mentioned peptide, alone or in combination with any other appropriate molecule, for example, anti-inflammatory steroid drugs (corticosteroids), disease modifiers drugs (methotrexate) or another cytokines antagonist used in Rheumatoid Arthritis treatment and use of this peptide to inhibit binding of IL-15 to receptor α subunit either soluble or in membrane-associated forms.

Peptide in current invention has a lineal structure and is mainly characterized by its capability to antagonize IL-15. On the other hand, the in vitro effect produced by the peptide in current invention is demonstrated by a CTLL-2 cell proliferation assay and by inhibition of TNFα-induced apoptosis assay.

For definition of described peptide it was used a mapping technique on a cellulose filter that contains IL-15 complete sequence in 10 aa consecutive peptides with 5 overlapping amino acids.

In current invention peptide Sec. No. 1 was chemically synthesized by solid phase technique, purified by HPLC, analyzed by mass spectrometry and finally evaluated in respect to its effect on IL-15 activity.

Results shown in current invention indicates that identified and synthesized region as a peptide of 10 aa (Sec. No.1) corresponds to an IL-15 region interacting with the receptor α subunit and therefore, interferes with IL-15 binding to its receptor inhibiting IL-15-induced T cell proliferation activity. Peptide (Sec. No. 1) comprising amino acids of IL-15 interacting with IL-15Rα mimics IL-15 protection effect of TNFα-induced apoptosis, which is mediated by binding of IL-15 to IL-15Rα (Bulfone-Paus et al., The FASEB Journal, 1999, September Vol. 13).

Results obtained here suggest its use as a therapeutic tool in the treatment of aforementioned IL-15 high expression-associated diseases, where it is justified use of IL-15 antagonists and in those pathologies where an apoptosis protection effect is needed as well as in soluble IL-15Rα high expression-associated pathologies. Likewise, antibodies which recognize a region comprised in Sec. No.1 in IL-15 will inhibit binding of IL-15 to IL-15Rα and will show an IL-15 antagonist activity by inhibiting binding of the molecules to such receptor subunit, for this reason a peptide coupled to a carrier molecule or MAP (multi-antigenic peptide) chemical conjugate could be used for obtaining IL-15 antagonist antibodies.

The aim of current invention is also applied to DNA encoding for aforementioned peptide. A vector containing a DNA sequence coding for the peptide in current invention may be also used as an alternative for expression of the peptidic sequence.

Peptide described here can be used in combination with another anti-inflammatory and immune-suppressors agents or others cytokines antagonists used in Rheumatoid Arthritis, Psoriasis, Chron's disease, etc. The peptide described can be included in therapeutic vaccines to elicit an anti-IL-15 humoral response.

Invention essence

Current invention consists in identification of an IL-15 sequence (Sec. No.1) interacting with receptor α subunit. Such sequence synthesized as a lineal 10 amino acids peptide shows IL-15 antagonist capacity concerning induction of T cell proliferation and an agonist effect concerning protection from TNFα-induced apoptosis.

BRIEF DRAWINGS DESCRIPTION

FIG. 1: IL-15R mapping on cellulose filter.

IL-15Rα-Fc recognizes peptide 8 corresponding to SEQ ID NO: 1 and to a lesser extent peptide 7

FIG. 2: Colorimetric assay in Tentagel S beads.

It was observed color development in beads containing SEQ ID NO: 1 peptide incubated with IL-15Rα-Fc (R&D) at 5 µg/mL 2a) Incubation of resin containing a) non-related peptide or b) peptide SEQ ID NO: 1 with containing resin incubated with 15Rα-Fc (R&D).

2b) Incubation of resin containing peptide SEQ ID NO: 1 with IL15Rα-Fc (R&D) (a) or peptide SEQ ID NO: 1, IL15Rα-Fc (R&D) in presence of an excess of IL-15 (b).

FIG. 3: CTLL-2 proliferation assay with human IL-15 (R&D) with a specific activity of $10^8$ Ul/mg 3a) CTLL-2 assay at different IL-15 concentrations and a fixed peptide concentration of 260 µM.

3b) CTLL-2 assay at different peptide SEQ ID NO: 1 concentrations and a fixed IL-15 concentration of 300 pg/mL.

FIG. 4: Apoptosis induction assay in the L929 cell line.

Cells were incubated with TNFα (100 ng/mL) alone or in combination with peptide SEQ ID NO: 1 (260 µM)

EXAMPLES FOR REALIZATION

The following examples are provided to illustrate current invention embodiments

Example 1

A. Identification of binding region to IL-15Rα

Synthesis of 10-mer peptides on cellulose support corresponding to the amino acid sequence of IL-15

To identify IL-15 regions involved in IL-15Rα binding, the peptide spot synthesis approach was used as previously described Frank et. al. The derivation of Whatman 540 paper was carried out estherifying the first anchor component, Fmoc-β-Ala-OH, using N,N'-Diisopropylcarbodiimide (DIC) and N-methylimidazole (NMI) in dry N,N-dimethylformamide (DMF). The spot array on the cellulose membrane was defined anchoring the Fmoc-β-Ala-OH on the previously marked positions, according to the required number of 10-mer peptides (22 peptides, overlapping in 5 residues, 114 amino acids of IL-15 sequence). Besides, a non-related 10 amino acids peptide was synthesized on spot 23 and also on spot 24 only Fmoc-β-Ala-OH was anchoring, both as controls. For the assembly of all these molecules, the standard Fmoc-/tBu chemistry was used. After the final cycle of synthesis, the N-terminus and side chains of all peptides were de-protected.

Binding of anti-IL-15 Abs to peptides synthesized on cellulose support

Cellulose sheet was soaked in ethanol to prevent possible hydrophobic interactions between the peptides on it. Ethanol was exchanged against Tris-buffer saline (TBS) (150 mM NaCl, 10 mM Tris, pH 7.6) by sequential washing. Nonspecific binding was blocked by incubating membrane overnight in 10 mL of TBS blocking buffer (5% Powdered milk in TBS). The sheet was subsequently incubated for 3 hours with IL-15 α-Receptor, diluted in 10 mL of T-TBS sample buffer (5% Powdered milk, 0.5% Tween-20 in TBS). For serum, 1:50 dilution was used. IL-15 α-Receptor was prepared at 5 μg/mL, in the same buffer solution. Cellulose sheet was washed four times with T-TBS buffer. Then an alkaline phosphatase conjugate anti-IgG (Fc specific) (Sigma) was added, diluted in T-TBS sample buffer, for 1 hour (1:25000 dilution for anti-human IgG in IL-15 α-Receptor assay. The cellulose sheet was washed four times again, with T-TBS and detection of peptide bound was achieved by incubating the membrane with 0.5 mg/mL of 5-Bromo 4-Chloro 3-Indolyl Phosphate (BCIP) (Sigma) in substrate buffer (100 mM NaCl, 2 mM $MgCl_2$, 100 mM Tris, pH 8.9). Positive spots developed a blue/violet color. Washing with PBS stopped staining. Cellulose sheet was finally regenerated for others assays as previously described (Frank, R. (1992) *Tetrahedron* 48, 9217). We observed the recognition of two peptides, 8 and 7. As experimental control the membrane was incubated with a humanized monoclonal antibody containing Fc region of the human IgG1. In this case we did not observe recognition of any peptide on the membrane.

Beads colorimetric assay demonstrating peptide binding to IL-15Rα Synthesis of peptide Sec. No.1 on $NH_2$-Tentagel-S resin The resin $NH_2$-Tentagel-S (0.24 mmol/g) was washed several times with di-chlorometane (DCM) and methanol. Then, it was incubated in a trifluoroacetic acid (TFA) solution 30% for 10 minutes; washed several times with DCM and incubated in di-isopropilethilamine (DIEA) 5% in DCM for 1 minute. This procedure activated the $NH_2$ groups for synthesis. Later, it was washed with DCM and incubated in di-methylformamide (DMF) for 5 minutes to synthesize the peptide. The conventional Fmoc/tBu strategy of synthesis was used. Coupling reactions were followed by ninhidrine test. Once peptide Sec. No.1 sequence was completed, amino acids side chains were de-protected, leaving it anchored by its C-terminal to the resin.

Assay on beads

Resin beads with anchored peptide were several times washed with saline solution (PBS). Non specific interactions were blocked with BSA (1%) in PBS for 1 hour at RT. Then, they were incubated with IL-15Rα-Fc fusion protein (R&D 147-IR) at 5 μg/mL in BSA (1%/PBS) for 16 hours at 4° C. Later, beads were washed in PBS three fold for 5 minutes with shaking and then incubated with anti-Fc IgG human-phosphatase conjugate diluted 1:25000 in BSA (1%/PBS) for three hours at RT. They were extensively washed with a saline solution (TBS/Tween-20, 1%) and incubated with BCIP (0.45 mg/mL) in substrate solution (100 mM Tris, pH 8.9; 100 mM NaCl; 2 mM MgCl2) for approximately 30 minutes. They were washed four fold with PBS to stop reaction. An intense blue color was only observed when resin-containing Sec. No. 1 peptide was incubated with the IL-15Rα-Fc protein and not when a resin containing a non related peptide was incubated with IL-15Rα-Fc. In that case, the chromogen substrate does not precipitate and do not develop color. Likewise, we did not observed color in presence of an excess of human IL-15.

Peptides Synthesis

The peptides were synthesized by Fmoc/tBu strategy, utilizing Fmoc-AM-MBHA resin at 0,54 mmol/g and synthesis protocols with mechanical shaking. After TFA treatment, the peptide was lyophilized and tested by HPLC-MS Example 2

Effect of described peptides on CTLL2 cell line proliferation

The cytokine-dependent cell line CTLL-2 proliferates in presence of IL-15. IL-15 bound molecules impairing receptor depending signal transduction would inhibit this cell line proliferation.

To evaluate the neutralizing capacity the peptide of the present invention, serial dilutions of them were done in 96 well plates (Costar, USA) in 25 μL volume of RPMI medium (Gibco) supplemented with 10% fetal bovine serum (Gibco). Previously washed CTLL-2 cells were added to $5 \times 10^3$ cells/well and it was incubated for 30 min. Then, 300 pg of IL-15 were added to each well. Plate was incubated for 72 h at 5% $CO_2$ and 37° C. The results are shown in FIG. 3b. We observed that peptide referred as SEQ ID NO: 1 inhibited the IL-15 induced proliferation with an $IC_{50}$ of 130 μM To measure proliferation MTT mitochondrial staining was used (Cosman et al. 1984, Nature, 312: 768-771). We also evaluated the antagonist effect of 260 μM of this peptide at different IL-15 concentrations (FIG. 3a). The inhibitory effect of peptide was dependent on IL-15 doses.

Example 3

Apoptosis induction in L929 cells

The DNA Fragmentation Assay allows to determine the amount of DNA that is degraded upon treatment of cells with TNF-alpha. The cells' DNA is radioactively labeled by growing the cells in presence of 3H-Thymidine so that radioactive 3H-Thymidine is incorporated into the DNA. After 24 h the cells were treated with Tripsin/EDTA, washed and seeded at 5000 cells per well in a 96 well plate. Then, the labeled cells were incubated with TNFα (100 ng/mL), IL-15 (100 ng/mL), peptides (260 μM) or combinations of TNFα with different peptides.

During this incubation the added agent (e.g. TNFα induces cells to die by apoptosis and consequently the fragmentation of DNA while the DNA of untreated cells remains intact).

After 24 h the cells were harvested: during harvesting, the cells were washed out of the wells of the 96 well plate with bidestilated water: the cells and organelles burst and the cell's DNA is set free. The cell fragments and DNA are passed through a filter membrane (glassfiber). Only particles of smaller than 1,5 µm can pass the filter. So, intact DNA (with a fragment length in the range of milimeters or even centimeters) will not be able to pass the filter but be collected on the filter membrane. DNA that was cleaved/degraded into fragments of about 5000 bp or less will be small enough to pass the pores of the filter and won't be collected on the filter. The filter membrane was dried and the amount of radioactivity (what corresponds to the amount of intact DNA) counted in a scintillation counter. The percentage of DNA fragmentation was calculated by comparing the counted radioactivity (counts per minute=cpm) of cells that were not treated with the cpm in cells that were treated with agent. As result we observed that the peptide Sec.No.1 protected form TNF induced apoptosis.

Example 4
Monoclonal antibodies preparation

The monoclonal antibodies were obtained as described by Georges Kohler and Cesar Milstein (Nature, 256:495-497, 1975). The peptide SEQ ID NO: 1 conjugated to KLH or a chemical conjugate containing 4 molecules of this peptide were used to raised monoclonal antibodies than bind and inhibit IL-15 activity.

Mice were immunized subcutaneously with a conjugated peptide that was prepared for injection by emulsifying with Freund's adjuvant in amount of 10 to 100 µg, followed by every other week subcutaneous immunizations with peptide in incomplete Freund's adjuvant. The immune response to IL-15 was monitored by ELISA. Mice with sufficient titer of anti-IL-15 immunoglobulin were boosted intravenously 3 days before sacrifice and removal of the spleen. To generate hybridomas producing monoclonal antibodies to IL-15 we used the refereed protocol published in Nature, 256:495-497, 1975.The resulting hybridomas were screening for the production of specific antibodies to IL-15 or peptide by ELISA and by inhibitory effect on IL-15 activity in CTLL-2 assay. Positive clones were inoculated into the peritoneal cavity of syngenic mice to produce ascitis and resulting monoclonal antibody was purified by ammonium sulphate precipitation and affinity chromatography based in the binding of the antibody to the protein A from *Staphylococcus aureus*.

Example 5

Evaluation of the peptide SEQ ID NO: 1 in the generation of neutralizing antibodies in Macacus irus monkeys Three groups were evaluated in a monkey's immunization scheme, immunized with a peptide conjugated to a carrier protein, chemically-conjugated peptide as a tetramer (MAP); and placebo. The proteins were administered in amounts of 100 µg to 200 µg per inoculation in Freund's adjuvant. Second immunization was done one month later and third immunization was done two months later. Two week after second and third immunization blood was extracted to evaluate level of anti-IL15 antibodies in the monkeys' sera. The neutralizing capacity of antibodies present in monkeys' sera was tested by CTLL-2 assay at the present of 300 pg of IL-15.

Advantages of the proposed solution

Peptide SEQ ID NO: 1 selectively inhibits binding of IL-15 to IL-15Rα.

Peptide SEQ ID NO: 1 antagonizes IL-15-induced proliferation effect on T cells (CTLL-2 cells) and besides, it is an agonist of the IL-15 apoptosis protective effect on cells sensitive to TNFα-induced apoptosis.

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Sep. 30, 2008. The sequence listing.txt file is 1 kb in size.

---

---

The invention claimed is:

1. An isolated IL-15 activity antagonist peptide consisting of the amino acid sequence set forth in SEQ ID NO: 1.

2. The peptide according to claim 1, wherein the peptide binds to an IL-15Rα cellular subunit or its soluble fraction.

3. The peptide according to claim 1, wherein the peptide inhibits IL-15-dependent T cell proliferation activity.

4. The peptide according to claim 1, being obtained by genetic manipulation or by chemical synthesis.

5. An isolated nucleic acid encoding the peptide of claim 1, wherein the peptide is capable of binding cellular IL-15Rα or its soluble fraction and inhibiting IL-15-dependent T cell proliferation activity.

6. An expression vector comprising a nucleic acid encoding the peptide of claim 1, wherein said peptide is capable of inhibiting IL-15-dependent T cell proliferation activity.

7. A method of treating rheumatoid arthritis in a mammal, comprising administering an effective amount of an isolated IL-15 activity antagonist peptide consisting of the amino acid sequence set forth in SEQ ID NO: 1 to the mammal.

8. A method of treating psoriasis in a mammal, comprising administering an effective amount of an isolated IL-15 activity antagonist peptide consisting of the amino acid sequence set forth in SEQ ID NO:1 to the mammal.

9. An immunogenic composition comprising a peptide according to claim 1 which inhibits IL-15-dependent T cell proliferation activity.

* * * * *